(12) United States Patent
Shah et al.

(10) Patent No.: US 6,423,304 B1
(45) Date of Patent: Jul. 23, 2002

(54) DIMERIZED FATTY ACID BASED POLYAMIDES USEFUL FOR CLEAR CANDLE AND GEL APPLICATIONS

(75) Inventors: Shailesh Shah, Dresher, PA (US); Sobhy El-Hefnawi, Mt. Holly, NJ (US); Douglas C. Rhubright, Harleysville, PA (US)

(73) Assignee: Cognis Corporation, Gulph Mills, PA (US)

(*) Notice: Subject to any disclaimer, the term of this patent is extended or adjusted under 35 U.S.C. 154(b) by 0 days.

(21) Appl. No.: 09/880,521

(22) Filed: Jun. 13, 2001

Related U.S. Application Data

(60) Provisional application No. 60/211,833, filed on Jun. 15, 2000.

(51) Int. Cl.[7] .............................. A61K 7/32; A61K 7/34; A61K 7/38; C08G 63/00; C08G 67/00; C08G 69/08; C08G 73/10; C08L 77/00
(52) U.S. Cl. .............................. 424/65; 424/66; 424/68; 424/400; 424/401; 44/265; 44/272; 44/275; 44/459; 431/288; 431/289; 431/291; 524/219; 524/606; 528/272; 528/288; 528/292; 528/302; 528/324; 528/326; 528/339; 528/339.3; 528/344
(58) Field of Search .................. 44/265, 272, 275, 44/459; 424/65, 66, 68, 400, 401; 431/288, 289, 291; 524/219, 606; 528/272, 288, 292, 302, 324, 326, 339, 339.3, 344

(56) References Cited

U.S. PATENT DOCUMENTS

| | | |
|---|---|---|
| 2,955,121 A | 10/1960 | Myers et al. |
| 3,148,125 A | 9/1964 | Strianse |
| 3,412,039 A | 11/1968 | Miller |
| 3,507,890 A | 4/1970 | Dieckelmann et al. |
| 3,615,289 A | 10/1971 | Felton |
| 3,645,705 A | 2/1972 | Miller et al. |
| 4,275,054 A | 6/1981 | Sebag et al. |
| 4,452,931 A | 6/1984 | Okamoto et al. |
| 4,937,069 A | 6/1990 | Shin |
| 5,069,897 A | 12/1991 | Orr |
| 5,102,656 A | 4/1992 | Kasat |
| 5,500,209 A | 3/1996 | Ross et al. |
| 5,538,718 A | 7/1996 | Aul et al. |
| 5,998,570 A | 12/1999 | Pavlin et al. |
| 6,111,055 A | 8/2000 | Berger et al. |

*Primary Examiner*—Shelley A. Dodson
(74) *Attorney, Agent, or Firm*—John E. Drach

(57) ABSTRACT

Blooming and/or syneresis in gel formulations can be reduced or eliminated by adding to an organic mixture an effective amount of a polyamide gelling agent having a softening point of less than about 105° C. wherein the polyamide is the reaction product of one or more diamines, optionally one or more mono-amines, one or more hydrogenated C36 dimer acids, optionally one or more $C_{2-22}$ dicarboxylic acids, and optionally one or more $C_{2-22}$ monocarboxylic acids.

9 Claims, No Drawings

DIMERIZED FATTY ACID BASED POLYAMIDES USEFUL FOR CLEAR CANDLE AND GEL APPLICATIONS

CROSS-REFERENCE TO RELATED APPLICATIONS

This application claims the benefit of abandoned provisional application Ser. No. 60/211,833, filed on Jun. 15, 2000, the entire contents of which are incorporated herein by reference.

STATEMENT REGARDING FEDERALLY SPONSORED RESEARCH OR DEVELOPMENT

Not Applicable.

BACKGROUND OF THE INVENTION

Polyamide gelling agents for use in transparent gel formulations such as transparent candles and personal care products such as clear deodorant gels have caused products into which they are added to exhibit blooming and syneresis. Known clear candle compositions utilizing commercially available polyamide resins such as VERSAMID® 940 or VERSAMID® 1655 as a gelling resin demonstrated poor long-term resistance to blooming and syneresis. Similar problems have occurred with clear gel personal products containing polyamide gelling agents and are described in U.S. Pat. No. 5,500,209, the Background of the Invention section of which is incorporated herein by reference.

SUMMARY OF THE INVENTION

The present invention pertains to a method for reducing or eliminating blooming and/or syneresis in a gel formulation comprising adding to an organic mixture an effective amount of a polyamide gelling agent having a softening point of less than about 105° C. wherein the polyamide is the reaction product of one or more diamines, optionally one or more mono-amines, one or more hydrogenated C36 dimer acids, optionally one or more C2–22 dicarboxylic acids, and optionally one or more C2–22 monocarboxylic acids.

BRIEF DESCRIPTION OF THE SEVERAL VIEWS OF THE DRAWINGS

None

DETAILED DESCRIPTION OF THE INVENTION

The term "gel" as used herein is defined in Almdale et al. (Polymer Gels and Networks, Vol. 1, No. 5 (1993)) according to the following two criteria: (1) a substance that consists of two or more components, one of which is a liquid, present in substantial quantities; and (2) a gel is a soft material which is solid or solid-like. A gel can also be defined according to its rheological properties. Thus, the term "gel" applies to systems having a value G'(w) that is higher than its value of G"(w) at low frequencies. G'(w) is the storage modulus which exhibits a pronounced plateau at higher frequencies (on the order of 1–100 radians/second), and G"(w) is the loss modulus which is considerably smaller than the storage modulus in the plateau region. A gel is free-standing or self-supporting in that its yield value is greater than the sheer stress imposed by gravity.

The diamines that can be used to make the polyamides according to the invention are comprised of two or more aliphatic or cycloaliphatic, linear or branched, saturated or unsaturated diamines which when copolymerized with the acid moieties described herein will produce a polyamide resin having a softening point of less than about 105° C. Examples of the diamines that can be present in the diamine mixture include, but are not limited to, ethylene diamine, 1,2- and 1,3-propylene diamine, teramethylene diamine, hexamethylene diamine, octamethylene diamine, 1,2-diaminocyclohexane, 1,3-bis(aminomethyl)cyclohexane and combinations thereof. The diamines also include polyether diamines which can be poly(ethylene oxide) $\alpha,\omega$-diamine or poly(propylene oxide) $\alpha,\omega$-diamine or poly (ethylene-co-propylene oxide) $\alpha,\omega$-diamine of various molecular weights and as well poly(ethylene oxide) or poly(propylene oxide) monoamines and triamines. Polyether amines are commercially available as, for example, JEFFAMINE®™ polyether diamines, available from Huntsman Chemical.

The monoamines that can be used to make the polyamides according to the invention include any aliphatic or alicyclic, saturated or unsaturated, linear or branched chain monoamine having from $C_2$ to $C_{60}$ carbon atoms. Polyether monoamines are also included and are commercially available as, for example, JEFFAMINE®™ polyether monoamines, available from Huntsman Chemical.

The hydrogenated dimer acids are those made by polymerizing unsaturated mono- and polyunsaturated fatty acids or a mixture thereof. Such acids can be made by the processes described in U.S. Pat. Nos. 2,955,121; 3,412,039; and 3,507,890, the entire contents of each of which is incorporated herein by reference. Such dimer acids are commercially available as, for example, EMPOL® 1008, EMPOL® 1004, EMPOL® 1025, EMPOL® 1011, or EMPOL® 1062 dimer acid from Cognis Corporation, Cincinnati, Ohio.

The $C_{2-22}$ dicarboxylic acids can be one or a mixture of dicarboxylic acids having from 2 to 22 carbon atoms examples of which include, but are not limited to malonic acid, succinic acid, adipic acid, azelaic acid, dodecanedioc acid and octadecenedioc acid.

The $C_{2-22}$ monocarboxylic acids can be any aliphatic, saturated or unsaturated, linear or branched monocarboxylic acid having from 2 to 22 carbon atoms. Examples of such acids include, but are not limited to, capryic acid, lauric acid, palmitic acid, palmitoleic acid, oleic acid, linoleic acid, isostearic acid, arachidic acid and arachidonic acid.

A preferred polyamide resin is the reaction product of a hydrogenated dimer acid, stearic acid, azelaic acid, ethylene diamine, and a polypropyleneoxide diamine having a mole. Wt. of about 230. Another preferred polyamide resin is the reaction product of a hydrogenated dimer acid, stearic acid, azelaic acid, ethylene diamine, and hexamethylene diamine.

Candle formulations containing polyamide resin gelling agents according to the invention exhibit better color stability in the melt and better compatibility with other ingredients than standard candle formulations. These lower softening point resins allow for formulated gels that can melt and wick at lower temperatures resulting in less thermal degradation and less discoloration of the melt. Also, higher softening point resin result in formulated gels with higher melting points which can approach the flash point of the fragrance or other gel ingredients and cause flaring of the whole candle surface. While the softening point of the polyamide resins according to the invention are less than about 105° C., they are preferably between 65° C. to 95° C., even more preferable between 75° C. to 90° C. have unexpectedly been found to provide better compatibility and less syneresis and blooming.

The polyamide resins according to the invention can also be used in such products as air-freshener gels where the polyamide is used to gel a fragrance composition, but not for burning. Polyamides are known to have desirable fragrance release and can be used in air-fresheners where the material, unlike candles, do not require heat to release the fragrance. Such gels are known to release their desired fragrance more readily. Other uses of the polyamide resins according to the invention include gelling agents for personal care and cosmetics applications such as deodorant gels and lipstick respectively.

The polyamide resins according to the invention can also be used in personal care products, e.g., cosmetics such as eye make-up, lipstick, foundation make-up, costume make-up, as well as baby oil, make-up removers, bath oil, skin moisturizers, sun care products, lip balm, waterless hand cleaner, medicated ointments, ethnic hair care products, perfume, cologne, and suppositories. Formulations to prepare such materials are well known in the art. For example, U.S. Pat. Nos. 3,615,289 and 3,645,705 describe the formulation of candles. U.S. Pat. Nos. 3,148,125 and 5,538,718 describe the formulation of lipstick and other cosmetic sticks. U.S. Pat. Nos. 4,275,054, 4,937,069, 5,069,897, 5,102,656 and 5,500,209 each describe the formulation of deodorant and/or antiperspirant. Each of these U.S. Patents is hereby incorporated fully herein by reference.

The method according to the invention comprises the addition of a polyamide resin gelling agent to an organic mixture. The resulting mixture is a gel. The organic mixture is any combination of organic compounds that when mixed with a gelling agent form a gel. Such compounds include, for example, fatty alcohols and fatty acid esters including naturally occurring oils such as castor oil, peanut oil, safflower oil, sunflower oil, corn oil or cod liver oil and synthetic esters of mono and difunctional alcohols and fatty acids.

The amount of polyamide resin gelling agent that can be used in the process according to the invention is an effective amount which is any amount that will eliminate or reduce the amount of blooming and/or syneresis in the gel formed as a result of mixing the polyamide gelling agent and the organic resin. The effective amount will be readily ascertainable by one of ordinary skill in the art. Typically, the amount will be in the range of from about 10% by weight of the formulation to about 90% by weight of the formulation and preferably from about 25% by weight of the formulation to about 60% by weight of the formulation.

The following examples are meant to illustrate but not to limit the invention. Amounts are expressed as weight percent.

In examples 1–7 below, the organic acids and 0.005% $H_3PO_4$ catalyst were charged to a 1 liter resin kettle and heated to 180° F. under vacuum for 0.5 hour. Vacuum was broken under nitrogen, and the amines were added over 15 minutes, typically displaying a 20° to 30° C. exotherm. The mixture was heated to 440° F. over 2 hours under nitrogen sweep with stirring. The reaction was held at 440° F. for 1.5 hours after which vacuum (15 mm Hg) was applied. The reaction was held at 440° F. for 2 hours under vacuum. Vacuum was released under nitrogen and the molten resin was cooled to 390° F. before discharging onto a Teflon sheet.

EXAMPLE 1

81% EMPOL® 1062 hydrogenated dimer acid, 1.9% triple press stearic acid, 0.8% azelaic acid, 5.8% ethylene diamine, and 10.5% JEFFAMINE® D230 (polypropyleneoxide diamine having a mole. Wt. of about 230) were reacted at 440° F. for 1 hour under nitrogen flow and 3 hours at 440° F. under vacuum of 15 mm Hg.

| | |
|---|---|
| Ball & Ring Softening Point | 96° C. |
| Brookfield Viscosity (@160° C.) | 14 poise |
| Acid value | 13.0 |
| Amine value | 0.3 |

EXAMPLE 2

69.6% EMPOL® 1062 hydrogenated dimer acid, 11.3% triple press stearic acid, 0.4% azelaic acid, 2.6% ethylene diamine, and 16.2% hexamethylene diamine (70% aqueous) were reacted at 440° F. for 1 hour under nitrogen flow and 3 hours at 440° F. under vacuum of 15 mm Hg.

| | |
|---|---|
| Ball & Ring Softening Point | 88° C. |
| Brookfield Viscosity (@160° C.) | 6.5 poise |
| Acid value | 8.6 |
| Amine value | 0.4 |

EXAMPLE 3

72.1% EMPOL® 1062 hydrogenated dimer acid, 11.3% isostearic acid, 0.4% azelaic acid, 2.4% ethylene diamine, and 13.8% hexamethylene diamine (70% aqueous) were reacted at 440° F. for 1 hour under nitrogen flow and 3 hours at 440° F. under vacuum of 15 mm Hg.

| | |
|---|---|
| Ball & Ring Softening Point | 89° C. |
| Brookfield Viscosity (@160° C.) | 6.0 poise |
| Acid value | 6.1 |
| Amine value | 0.2 |

EXAMPLE 4

70.2% EMPOL® 1062 hydrogenated dimer acid, 11.3% triple press stearic acid, 0.4% azelaic acid, 3.8% ethylene diamine, 10.3% hexamethylene diamine (70% aqueous), and 4.0% JEFFAMINE® D230 (polyether diamine from Huntsman Chemical) were reacted at 440° F. for 1 hour under nitrogen flow and 3 hours at 440° F. under vacuum of 15 mm Hg.

| | |
|---|---|
| Ball & Ring Softening Point | 92° C. |
| Brookfield Viscosity (@160° C.) | 4.0 poise |
| Acid value | 4.0 |
| Amine value | 1.5 |

EXAMPLE 5

34.15% EMPOL® 1062 hydrogenated dimer acid, 15.56% triple press stearic acid, 33.84% isostearic acid, and 16.46% 1,2-diaminocyclohexane (mixture of cis and trans) were reacted at 440° F. for 1 hour under nitrogen flow and 3 hours at 440° F. under vacuum of 15 mm Hg.

| | |
|---|---|
| Ball & Ring Softening Point | 105° C. |
| Brookfield Viscosity (@160° C.) | 0.5 poise |

EXAMPLE 6

38.0% EMPOL® 1062 hydrogenated dimer acid, 19.2% triple press stearic acid, 25.1% isostearic acid, 1.9% ethylene diamine, and 15.8% of 1,3-bis(aminomethyl) cyclohexane were reacted at 440° F. for 1 hour under nitrogen flow and 3 hours at 440° F. under vacuum of 15 mm Hg.

| | |
|---|---|
| Ball & Ring Softening Point | 99° C. |
| Brookfield Viscosity (@160° C.) | 0.8 poise |

EXAMPLE 7

71.6% EMPOL® 1062 hydrogenated dimer acid, 4.7% ethylene diamine, 19.6% JEFFAMINE® XTJ505 and 4.2% hexamethylene diamine (70% aqueous) were reacted at 440° F. for 1 hour under nitrogen flow and 3 hours at 440° F. under vacuum of 15 mm Hg.

In examples 8–19 below, the compositions were prepared by combining the resin and both dry and liquid ingredients in a 100 ml flask and heating to 100° C. under a nitrogen blanket while stirring with a magnetic stir bar. Once homogeneous, the resin solutions were poured in aluminum dishes and allowed to cool.

Gel Ingredients:
- 90/95 HD-oleyl alcohol is a product of Cognis Corporation.
- GUERBITOL® 20 is isoarachidyl alcohol, a product of Cognis Corporation.
- GUERBITOL® 16 is isocetyl alcohol, a product of Cognis Corporation.
- EMERY® 3389 is isostearyl alcohol, a product of Cognis Corporation.
- SPEZIOL® 1070 is a hydrogenated C36 dimer diol, a product of Cognis Corporation.
- SPEZIOL® 1075 is a C36 dimer diol, a product of Cognis Corporation.
- EMPOL® 1008 is a C36 diacid, a product of Cognis Corporation.
- TEXAPRINT SSEH is a fatty acid ester, a product of Cognis Deutschland GmbH.
- TEXAPRINT SKEH is a fatty acid ester, a product of Cognis Deutschland GmbH.
- EDENOL® 9058 is 2-ethylhexyl azelate, a product of Cognis Corporation.
- EMEREST® 2326 is a butyl stearate, a product of Cognis Corporation.
- EMERY® 2218 is a methyl stearate, a product of Cognis Corporation.
- EMEREST® 2384 is a propylene glycol isostearate, a product of Cognis Corporation.
- EMEREST® 2712 is a PEG-8 distearate, a product of Cognis Corporation.
- PARACIN 220 is the N-(2-hydroxyethyl)-12-hydroxystearamide, a product of Caschem.
- AMIDOX L5 is an ethoxylated lauric acid amide, a product of Stepan.
- EMSORB® 2500 is a sorbitan monooleate, a product of Cognis Corporation.
- EMSORB® 2503 is a sorbitan trioleate, a product of Cognis Corporation.
- STANDAMID® KD is a cocamide-diethanol amine adduct, a product of Cognis Corporation.

EXAMPLE 8

14 g Resin from Example #1
14 g TEXAPRINT SSEH
14 g 90/95 HD-oleyl alcohol
6 g EMEREST® 2384

The mixture formed a stable, soft, clear gel which showed no blooming or syneresis.

EXAMPLE 9

COMPARATIVE EXAMPLE 14 g VERSAMID® 1655
14 g TEXAPRINT SSEH
14 g 90/95 HD-oleyl alcohol
6 g EMEREST® 2384

The mixture formed a slightly hazy gel which exhibited decreasing clarity over time and suffered from syneresis of liquids to the surface.

EXAMPLE 10

48 g Example #8
2 g EMERY® 2218 methylstearate

The blend resulted in a gel similar to the composition in Example #8 except with a higher melting point and a harder, less elastic gel.

EXAMPLE 11

48 g Example #8
2 g EMEREST® 2712

The blend resulted in a gel similar to the composition in Example #8 except with a higher melting point, a harder, less elastic gel and a very slight haziness.

EXAMPLE 12

45 g Resin from Example #4
20 g TEXAPRINT SSEH
15 g 90/95 HD-oleyl alcohol
10 g EMEREST® 2384
5 g AMIDOX L5

The mixture formed a stable, clear gel which did not exhibit syneresis or blooming.

EXAMPLE 13

50 g Resin from Example #4
10 g TEXAPRINT SSEH
25 g 90/95 HD-oleyl alcohol
15 g EMEREST® 2384
2 g EMSORB® 2500 Sorbitan monooleate The mixture formed a stable, clear gel which did not exhibit syneresis or blooming.

EXAMPLE 14

50 g Resin from Example #4
20 g TEXAPRINT SSEH 15 g 90/95 HD-oleyl alcohol
15 g EMEREST® 2384
2 g EMSORB® 2500 Sorbitan monooleate The mixture formed a stable, clear gel which did not exhibit syneresis or blooming and was harder than the gel in Example #13.

EXAMPLE 15

35 g Resin from Example #2
38 g TEXAPRINT SSEH
12 g 90195 HD-oleyl alcohol
12 g EMPOL® 1008
1 g EMSORB® 2500 Sorbitan monooleate The mixture formed a stable, clear soft gel.

EXAMPLE 16

35 g Resin from Example #2
38 g TEXAPRINT SSEH
24 g SPEZIOL® 1070
1 g EMSORB® 2500 Sorbitan monooleate The mixture formed a stable, clear soft gel.

EXAMPLE 17

35 g Resin from Example #4
38 g TEXAPRINT SSEH
12 g SPEZIOL® 1070
12 g EMPOL® 1008
1 g EMSORB® 2500 Sorbitan monooleate The mixture formed a stable, clear soft gel.

EXAMPLE 18

35 g Resin from Example #1
38 g TEXAPRINT SSEH
12 g GUERBITOL® 20
12 g EMPOL® 1008
0.5 g Azelaic acid
1 g EMSORB® 2500 Sorbitan monooleate
1 g EMSORB® 2503 Sorbitan monooleate The mixture formed a stable, clear soft gel.

EXAMPLE 19

35 g Resin from Example #2
8 g TEXAPRINT SSEH
16 g SPEZIOL® 1075
10 g PARACIN 220
3 g AMIDOX L5

The mixture formed a stable, clear hard gel.

What is claimed is:

1. A method for reducing or eliminating blooming and/or syneresis in a gel formulation comprising adding to an organic mixture an effective amount of a polyamide gelling agent having a softening point of less than about 105° C. wherein the polyamide is the reaction product of one or more diamines, optionally one or more mono-amines, one or more hydrogenated C36 dimer acids, optionally one or more $C_{2-22}$ dicarboxylic acids, and optionally one or more $C_{2-22}$ mono-carboxylic acids.

2. The method of claim 1 wherein the dicarboxylic acid is azelaic acid.

3. The method of claim 1 wherein the diamine is ethylene diamine.

4. The method of claim 1 wherein the diamine mixture is comprised of ethylene diamine and a polyether diamine.

5. The method of claim 1 wherein the diamine mixture is comprised of ethylene diamine and a hexamethylene diamine.

6. The method of claim 1 wherein the effective amount is from about 10% by weight to about 90% by weight of the formulation.

7. The method of claim 1 wherein the effective amount is from about 25% by weight to about 60% by weight of the formulation.

8. A method for reducing or eliminating blooming and/or syneresis in a gel formulation comprising adding to an organic mixture an effective amount of a polyamide gelling agent having a softening point of less than about 105° C. wherein the polyamide is the reaction product of a hydrogenated dimer acid, stearic acid, azelaic acid, ethylene diamine, and a polypropyleneoxide diamine having a mole. Wt. of about 230.

9. A method for reducing or eliminating blooming and/or syneresis in a gel formulation comprising adding to an organic mixture an effective amount of a polyamide gelling agent having a softening point of less than about 105° C. wherein the polyamide is the reaction product of a hydrogenated dimer acid, stearic acid, azelaic acid, ethylene diamine, and hexamethylene diamine.

* * * * *